(12) United States Patent
Mach-Aigner et al.

(10) Patent No.: US 10,106,827 B2
(45) Date of Patent: Oct. 23, 2018

(54) METHOD AND AGENTS FOR PRODUCING N-ACETYLNEURAMINIC ACID (NEUNAC)

(71) Applicant: TECHNISCHE UNIVERSITAT WIEN, Vienna (AT)

(72) Inventors: Astrid Mach-Aigner, Untertullnerbach (AT); Robert Mach, Untertullnerbach (AT); Matthias G. Steiger, Vienna (AT)

(73) Assignee: TECHNISCHE UNIVERSITÄT WIEN, Vienna (AT)

( * ) Notice: Subject to any disclaimer, the term of this patent is extended or adjusted under 35 U.S.C. 154(b) by 16 days.

(21) Appl. No.: 14/515,120

(22) Filed: Oct. 15, 2014

(65) Prior Publication Data
US 2015/0167038 A1    Jun. 18, 2015

Related U.S. Application Data

(62) Division of application No. 13/993,979, filed as application No. PCT/AT2011/000510 on Dec. 22, 2011, now abandoned.

(30) Foreign Application Priority Data

Dec. 22, 2010   (AT) ............................... A 2111/2010

(51) Int. Cl.
| | |
|---|---|
| *C12N 1/00* | (2006.01) |
| *C12N 15/63* | (2006.01) |
| *C12N 15/80* | (2006.01) |
| *C12P 19/26* | (2006.01) |
| *C12N 9/10* | (2006.01) |
| *C12N 9/90* | (2006.01) |
| *C12N 9/12* | (2006.01) |

(52) U.S. Cl.
CPC ............ *C12P 19/26* (2013.01); *C12N 9/1085* (2013.01); *C12N 9/1241* (2013.01); *C12N 9/90* (2013.01); *C12N 15/80* (2013.01); *C12Y 205/01056* (2013.01); *C12Y 501/03008* (2013.01); *C12Y 207/07043* (2013.01); *C12Y 501/03014* (2013.01)

(58) Field of Classification Search
None
See application file for complete search history.

(56) References Cited

U.S. PATENT DOCUMENTS

| | | | |
|---|---|---|---|
| 5,610,034 A | 3/1997 | Nyyssonen et al. | |
| 7,579,175 B2 | 8/2009 | Koizumi et al. | |
| 2004/0115790 A1* | 6/2004 | Pakula .................. | C12N 15/80 435/252.3 |
| 2004/0265953 A1* | 12/2004 | Harman ................. | C12N 15/52 435/69.1 |
| 2005/0142643 A1* | 6/2005 | Shiba ..................... | C12P 19/26 435/85 |
| 2006/0286637 A1* | 12/2006 | Hamilton ............. | C12N 9/2402 435/69.1 |

FOREIGN PATENT DOCUMENTS

| | | |
|---|---|---|
| EP | 0578825 A1 | 1/1994 |
| EP | 1081230 A2 | 3/2001 |
| EP | 1154018 A1 | 11/2001 |
| EP | 1484406 A1 | 12/2004 |
| WO | 94/29476 A1 | 12/1994 |
| WO | 2005/090552 A2 | 9/2005 |

OTHER PUBLICATIONS

"N-acetylneuraminate synthase" MESH entry. 1970. 2 pages.*
Acetylglucosamine MESH Entry, 1991, 2 pages.*
"N-Acylneuraminate-9-phosphate synthase" MESH Entry, 1970. 2 pages.*
Steiger et al., Synthesis of an antiviral drug precursor from chitin using a saprophyte as a whole-cell catalyst, Microbial Cell Factories, 10: 102 (Dec. 2011).
Blume et al., UDP-N-acetylglucosamine 2-epimerase/N-acetylmannosamine kinase, functionally expressed in and purified from *Escherichia coli*, yeast, and insect cells, Protein Expression and Purification, 35: 387-396 (2004).
Tabata et al., Production of N-acetyl-D-neuraminic acid by coupling bacteria expressing N-acetyl-D-glucosamine 2-epimerase and N-acetyl-D-neuraminic acid synthase, Enzyme and Microbial Technology, 30: 327-333 (2002).
Gruber et al., Cloning of the Trichoderma reesei pyrG gene and its use as a homologous marker for a high-frequency transformation system, Current Genetics, 18: 447-451 (1990).
Vann et al., Purification and characterization of the *Escherichia coli* K1 neuB gene product N-acetylneuraminic acid synthase, Glycobiology, 7: 697-701 (1997).
Written Opinion of the International Searching Authority for International Application No. PCT/AT2011/000510 dated Jun. 22, 2013.
English Translation of the Written Opinion of the International Searching Authority for International Application No. PCT/AT2011/000510 dated Jun. 22, 2013.
U.S. Office Action from U.S. Appl. No. 13/993,979, dated Jul. 15, 2014.
U.S. Office Action from U.S. Appl. No. 13/993,979, dated Dec. 18, 2013.
U.S. Office Action from U.S. Appl. No. 13/993,979, dated Oct. 22, 2013.

* cited by examiner

*Primary Examiner* — Christopher M Babic
*Assistant Examiner* — Kimberly A. Aron
(74) *Attorney, Agent, or Firm* — Nevrivy Patent Law Group P.L.L.C.

(57) ABSTRACT

The invention relates to an isolated nucleic acid molecule comprising at least one promoter that is active in fungal cells of the *trichoderma* species, wherein a nucleic acid sequence encoding an N-acetylglucosamine-2-epimerase and/or an N-acetylneuraminic acid synthase is operatively bound to each promoter. The at least one promoter that is active in fungal cells is a constitutive promoter.

18 Claims, 5 Drawing Sheets
Specification includes a Sequence Listing.

METHOD AND AGENTS FOR PRODUCING N-ACETYLNEURAMINIC ACID (NEUNAC)

CROSS-REFERENCE TO RELATED APPLICATIONS

This application is a divisional of U.S. patent application Ser. No. 13/993,979, which application is a § 371 national phase of International Patent Application No. PCT/AT2011/000510, filed Dec. 22, 2011. The content of the foregoing application is incorporated by reference herein in its entirety.

REFERENCE TO A SEQUENCE LISTING SUBMITTED

The content of the sequence listing (filename: 2014-10-15_SeqL_SAP-008US2_ST25.txt, size: 8,748 bytes, date of creation: Oct. 15, 2014) electronically submitted via EFS-Web is incorporated herein by reference in its entirety.

The present invention relates to methods and means for producing N-acetylneuraminic acid (NeuNAc).

N-acetylneuraminic acid (NeuNAc) pertains to the group of sialic acids. In mammals, sialic acids are usually present as a terminal residue of sugar conjugates on the cell surface. Due to their terminal position and the negative carboxylation function sialic acids play an important role in cellular recognition and adhesion processes.

Derivatives of NeuNAc are employed as neuraminidase inhibitors for the treatment of viral infections, such as influenza. NeuNAc serves as a starting material for the manufacture of such medicaments, such as oseltamivir and zanamivir. NeuNAc may either be extracted from corresponding raw materials, such as milk and eggs, or chemically synthesized. At present, NeuNAc is made exclusively from raw materials, such as N-acetylglucosamine, wherein a proportion of the known methods comprise enzymatically catalyzed steps.

Document EP 1 154 018 A1 describes an N-acetylglucosamine 2-epimerase having a specific amino acid sequence. According to this European patent application, said epimerase can be recombinantly produced in various host cells, i. a. in yeasts, wherein expression vectors can be used which have a promoter operably linked to a nucleic acid molecule encoding N-acetylglucosamine 2-epimerase.

Document EP 1 484 406 A1 describes a method for producing N-acetylneuraminic acid. In this context, a variety of inducible promoters are mentioned which are capable of controlling the expression of the enzymes required for the production of N-acetylneuraminic acid.

Document WO 94/29476 describes a method for the production of NeuNAc in which N-acetyl-D-glucosamine is initially converted to N-acetyl-D-mannosamine by epimerization. The product obtained in this first step is then reacted with pyruvate and a NeuNAc aldolase to form NeuNAc.

Documents U.S. Pat. No. 7,579,175 and EP 1 081 230 A2 each describe a method for the production of NeuNAc, wherein microorganisms which exhibit a NeuNAc synthetase activity and bacteria, such as e. g. E. coli, which are capable of synthesizing phosphoenol pyruvic acid, are cultivated in a medium containing N-acetylmannosamine and glucose or fructose.

Alternatively to the methods mentioned in the above, document EP 0 578 825 discloses a process for the production of NeuNAc in which N-acetylglucosamine and pyruvic acid are reacted with N-acetylneuraminic acid lyase.

The disadvantage of the methods described in the above is that they are usually equilibrium reactions in which an excess of pyruvate must be employed to shift the equilibrium reaction toward NeuNAc. Furthermore, the N-acetylglucosamine used in these reactions is too expensive to allow for an inexpensive production of NeuNAc. It is therefore an object of to the present invention to provide a method which overcomes the aforementioned disadvantages.

The present invention relates to an isolated nucleic acid molecule comprising at least one promoter that is active in fungal cells of the genus *Trichoderma* and has a nucleic acid sequence encoding an N-acetylglucosamine 2-epimerase and/or an N-acetylneuraminic acid synthase operably linked thereto, wherein said at least one promoter that is active in fungal cells is a constitutive promoter.

According to the present invention it was found that NeuNAc can be produced in a simple and efficient manner in a fungal cell of the genus *Trichoderma*, provided said fungal cell is capable of constitutively expressing N-acetylglucosamine 2-epimerase and N-acetylneuraminic acid synthase. The fungal cell used herein should also be capable of providing a sufficient amount of N-acetyl-D-glucosamine in order to produce N-acetyl-D-mannosamine with the aid of the N-acetylglucosamine 2-epimerase, wherein NeuNAc is eventually synthesized by the reaction of N-acetyl-D-mannosamine and the N-acetylneuraminic acid synthase. Of course, it would also be possible to use fungal cells which are not capable of providing N-acetyl-D-glucosamine. In such a case, N-acetyl-D-glucosamine would have to be added to the culture medium or organisms would have to be used that are capable of providing N-acetyl-D-glucosamine to the medium.

Since naturally occurring fungal cells are not capable of expressing N-acetylglucosamine 2-epimerase and N-acetylneuraminic acid synthase, corresponding nucleic acid molecules comprising the corresponding nucleic acid sequences have to be introduced into the fungal cells used. In this process, the nucleic acid molecule to be introduced may comprise the nucleic acid sequences of both enzymes. Alternatively, it is also possible to introduce two nucleic acid molecules into the fungal cell, wherein one molecule encodes N-acetylglucosamine 2-epimerase and the other molecule encodes N-acetylneuraminic acid synthase. It is, however, prerequisite that both molecules are constitutively expressed in the host cell.

In order to enable the constitutive expression of both enzymes, the encoding nucleic acid sequences thereof are operably linked to a promoter that acts constitutively in fungal cells.

According to the present invention, the term "operably linked to" means that the nucleotide sequence encoding the enzymes according to the present invention is bound to the regulatory sequence(s) such that the expression of the nucleotide sequence is possible and both sequences are linked together such that they fulfill the function that is predicted for and assigned to the sequence. A nucleic acid is "operably linked" if it is brought into a functional relationship with another nucleic acid sequence. Thus, a promoter is operably linked to a coding sequence if it affects the transcription of the sequence. Binding is accomplished by means of ligation at suitable restriction sites. If such sites do not exist, synthetic oligonucleotide adaptors are used according to conventional practice.

A "constitutive promoter" is a promoter that enables a gene or operon to be continuously expressed in a cell. A "constitutive promoter" is transcriptionally active in most stages of growth. In contrast, the expression rate of genes or operons which are operably linked to "inducible promoters" can be specifically controlled, so that under certain conditions the transcription is completely down-regulated and is up-regulated under different, preferably extrinsic, conditions.

N-acetyl-D-glucosamine 2-epimerase and N-acetylglucosamine 2-epimerase (EC 5.1.3.8), respectively, catalyze the conversion of N-acetylglucosamine to form N-acetylmannosamine. The coding nucleic acid sequence of this enzyme has been described, i. a., in mammals and bacteria, such as cyanobacteria, in which these enzymes are expressed. The corresponding nucleic acid sequences encoding these enzymes may be used according to the present invention. In order to improve the expression in fungal cells it is possible to generate codon-optimized nucleic acid sequences from an epimerase amino acid sequence, which are finally used in the nucleic acid molecule according to the present invention. It is particularly preferred to provide the N-acetylglucosamine 2-epimerase from *Anabaena* sp. (GenBank ABG57042) in the nucleic acid molecule according to the present invention and to express it in fungal cells.

In order to improve the expression of the enzymes mentioned in the above, it is advantageous to optimize the nucleic acid sequences with respect to their codon frequency in a host cell into which they are introduced. The codon optimization was carried out based on information on the frequency of the codons, e. g. in *Trichoderma reesei*. This information may be retrieved from the "Codon Usage Database" and the codon usage of *Trichoderma reesei* is given in Table 1.

TABLE 1

Codon usage in *Hypocrea jecorina* (*Trichoderma reesei*), e.g. based on the analysis of 118 CDSs (54050 codons)
Fields: [Triplet] [Frequency of occurrence per 1000] ([number])

| | | | |
|---|---|---|---|
| UUU 13.3 (719) | UCU 10.7 (580) | UAU 8.6 (463) | UGU 3.0 (164) |
| UUC 24.3 (1311) | UCC 20.4 (1101) | UAC 27.5 (1486) | UGC 10.6 (575) |
| UUA 0.7 (39) | UCA 6.4 (345) | UAA 0.9 (50) | UGA 0.5 (29) |
| UUG 7.9 (428) | UCG 16.0 (866) | UAG 0.7 (39) | UGG 16.7 (904) |
| CUU 9.4 (510) | CCU 12.3 (663) | CAU 5.3 (285) | CGU 5.5 (295) |
| CUC 29.9 (1617) | CCC 25.4 (1375) | CAC 17.7 (957) | CGC 17.4 (939) |
| CUA 2.3 (125) | CCA 6.9 (371) | CAA 8.7 (469) | CGA 7.3 (394) |
| CUG 27.3 (1473) | CCG 11.9 (641) | CAG 31.9 (1725) | CGG 5.6 (300) |
| AUU 16.0 (866) | ACU 10.7 (578) | AAU 8.3 (447) | AGU 3.9 (213) |
| AUC 31.0 (1676) | ACC 27.2 (1470) | AAC 38.4 (2077) | AGC 22.2 (1202) |
| AUA 2.1 (115) | ACA 7.5 (405) | AAA 4.6 (250) | AGA 2.9 (158) |
| AUG 20.1 (1085) | ACG 18.3 (987) | AAG 42.4 (2293) | AGG 5.2 (279) |
| GUU 11.2 (608) | GCU 18.0 (972) | GAU 15.8 (854) | GGU 14.0 (754) |
| GUC 36.9 (1992) | GCC 48.0 (2596) | GAC 41.0 (2214) | GGC 51.0 (2758) |
| GUA 2.4 (131) | GCA 10.5 (566) | GAA 10.2 (551) | GGA 13.3 (720) |
| GUG 14.8 (800) | GCG 14.2 (765) | GAG 38.0 (2052) | GGG 7 0 (378) |

N-acetylneuraminic acid synthase (EC 2.5.1.56) catalyzes the reaction of N-acetylmannosamine to form NeuNAc. In addition, this reaction involves phosphoenolpyruvate and water as a co-substrate. N-acetylneuraminic acid synthase is expressed in bacteria, such as *E. coli, Campylobacter jejuni* and *Neisseria meningitidis*. The corresponding nucleic and amino acid sequences are thus well known or identifiable to a sufficient extent. From the known sequences, it is possible to derive codon-optimized nucleic acid sequences which are transcribed and translated particularly well in fungal cells. It is particularly preferred to provide N-acetylneuraminic acid synthase from *Campylobacter jejuni* (e. g. *C. jejuni* NCTC11168) in the nucleic acid molecule according to the present invention and to express it in fungal cells.

According to a particularly preferred embodiment of the present invention, the N-acetyl-D-glucosamine 2-epimerase is encoded by the following nucleic acid sequence:

SEQ ID NO: 1
atgggcaagaacctccaggccctggcccagctctacaagaacgccctcct caacgacgtcctgcccttctgggagaaccacagcctcgacagcgagggcg gctacttcacctgcctcgaccgccagggcaaggtctacgacaccgacaag ttcatctggctccagaaccgccaggtctggaccttcagcatgctctgcaa ccagctggagaagcgcgagaactggctcaagatcgcccgcaacggcgcca agttcctcgcccagcacggccgcgacgacgagggcaactggtactttgcc ctgaccgcggcggcgagcctctggtccagccctacaacatcttcagcga ctgcttcgccgccatggccttcagccagtacgccctcgccagcggcgagg agtgggccaaggacgtcgccatgcaggcctacaacaacgtcctccgccgc aaggacaaccccaagggcaagtacaccaagacctaccccggcacccgccc catgaaggccctggctgtccccatgatcctcgccaacctcaccctggaga tggagtggctcctcccccaggagaccctggagaacgtcctcgccgccacc gtccaggaggtcatgggcgacttcctcgaccaggagcagggcctcatgta cgagaacgtcgcccccgacggcagccacatcgactgcttcgagggccgcc tcatcaacccggccacggcatcgaggccatgtggttcatcatggacatc gcccgccgcaagaacgacagcaagaccatcaaccaggccgtcgacgtcgt cctcaacatcctcaacttcgcctgggacaacgagtacggcggcctctact acttcatggacgccgccggccaccccccagcagctggagtgggaccag aagctctggtgggtccacctggagagcctcgtcgccctcgccatgggcta ccgcctcaccggccgcgacgcctgctgggcctggtatcagaagatgcacg actacagctggcagcacttcgccgaccctgagtacggcgagtggttcggc tacctcaaccgccgaggcgaggtcctcctcaacctcaagggcggcaagtg gaagggctgcttccacgtccccgcgccatgtacctctgctggcagcagt tcgaggccctcagctaa According to a further preferred embodiment of the present invention, the N-acetylneuraminic acid synthase is encoded by the following nucleic acid sequence:

(SEQ ID NO: 2)
atgcagatcaagatcgacaagctcaccatcagccagaagaaccccctcat catccccgagatcggcatcaaccacaacggcagcctggagatcgccaagc tcatggtcgacgccgcaagcgagccggcgccaagatcatcaagcaccag acccacatcgtcgaggacgagatgagccaggaggccaagaacgtcatccc cggcaacgccaacatcagcatctacgagatcatggagcagtgcgccctca actacaaggacgagctggccctcaaggagtacgtcgagaagcagggcctc gtctacctcagcacccccttcagccgcgccgccgccaaccgcctggagga catgggcgtcagcgcctacaagatcggcagcggcgagtgcaacaactacc -continued

```
ccctgatcaagcacatcgcccagttcaagaagcccatgatcatcagcacc ggcatgaacagcatcgagagcatcaagcccaccgtcaagatcctccgcga ctacgagatcccttcgtcctcctgcacaccaccaacctctaccccaccc ccagccacctcgtccgcctccaggccatgctggagctgtacaaggagttc aactgcctctacggcctcagcgaccacacgacgaacaacctcgcctgcat cggcgccatcgccctcggcgccagcgtcctggagcgccacttcaccgaca ccatggaccgcaagggccccgacatcgtctgcagcatggacgagagcacc ctcaaggacctcatcaaccagacccaggagatggtcctcctccgcggcga caacaacaagaacccctgaaggaggagcaggtcaccatcgacttcgcct tcgccagcgtcgtcagcatcaaggacatcaagaagggcgagatcctcagc atggacaacatctgggtcaagcgccccagcaagggcggcatcagcgccaa ggacttcgaggccatcctcggcaagcgcgccaagaaggacatcaagaaca acatccagctcacctgggacgacttcgagtaa
```

The fungal cells according to the present invention pertain to the genus Trichoderma.

Fungal cells of the genus Trichoderma are particularly useful in the biosynthesis of NeuNAc as the members of this genus are capable of providing a sufficient amount of N-acetyl-D-glucosamine.

According to a particularly preferred embodiment of the present invention, the fungal cells are Trichoderma reesei cells.

According to a preferred embodiment of the present invention, the constitutive promoter is selected from the group consisting of promoters of the glycolysis genes, in particular pki, gpd or zwf1, tef1a, act, cox4, neg1 and sar1.

A further aspect of the present invention relates to a vector comprising a nucleic acid molecule according to the present invention.

A still further aspect of the present invention relates to a fungal cell of the genus Trichoderma comprising a nucleic acid molecule or a vector according to the present invention.

Into the fungal cell according to the present invention, one or more nucleic acid molecules or vectors comprising nucleic acid sequences encoding N-acetylglucosamine 2-epimerase and N-acetylneuraminic acid synthase can be introduced. The regions encoding the enzymes are operably linked to a constitutive promoter.

The nucleic acid molecule or the vector according to the present invention are introduced into the host cell using generally known methods.

The fungal cell according to the present invention pertains to the genus Trichoderma. By degradation of chitin, members of the genus Trichoderma are capable of providing N-acetylglucosamine in an amount that is sufficient for synthesizing a sufficient amount of NeuNAc with the aid of recombinantly expressed N-acetylglucosamine 2-epimerase and N-acetylneuraminic acid synthase. Therefore, the use of fungal cells of this genus is particularly preferred according to the present invention.

If chitin is used as a starting substance, it is reduced to form N-acetylglucosamine. This monomer may be used as both a carbon and a nitrogen source for cell growth and also as a building block for the cell wall biosynthesis (a substantial component is chitin) as well as for the synthesis of N-acetyl neuraminic acid. An inducible system will come into action in a selective manner and thus cause an overload with respect to the availability of N-acetylglucosamine. In contrast, a constitutive system will continuously withdraw N-acetylglucosamine and therefore enable a continuous product formation.

According to a particularly preferred embodiment of the present invention, the fungal cell is Trichoderma reesei.

The fungal cell according to the present invention comprises at least one nucleic acid molecule whose nucleic acid sequence encodes an N-acetylglucosamine 2-epimerase and an N-acetylneuraminic acid synthase and is operably linked to a constitutive promoter that is active in fungal cells.

A further aspect of the present invention relates to a method for producing N-acetylneuraminic acid (NeuNAc), comprising the cultivation of fungal cells according to the present invention in the presence of an N-acetyl-D-glucosamine source.

In order to produce NeuNAc using an N-acetylglucosamine 2-epimerase and an N-acetylneuraminic acid synthase, N-acetyl-D-glucosamine is required as a substrate. Therefore, it is necessary to use fungal cells that are capable of providing this substrate.

According to a preferred embodiment of the present invention, the N-acetyl-D-glucosamine source is chitin.

DESCRIPTION OF DRAWINGS

The present invention is illustrated in more detail in conjunction with the following Figures and Examples, without being limited thereto.

Figure 1:
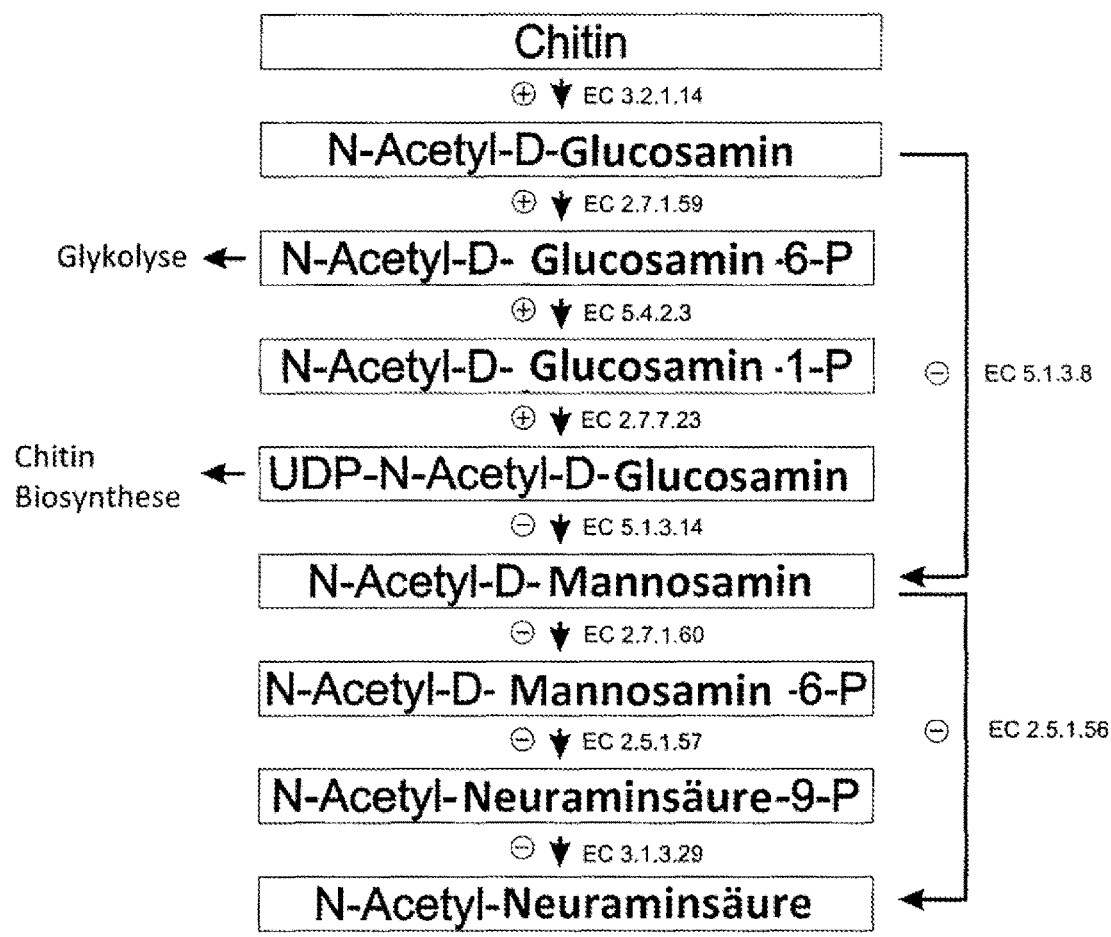
FIG. 1 shows an overview of possible metabolic reaction pathways, from the polymer chitin as a starting substance to the formation of NeuNAc. Metabolic intermediate products are shown in rectangles and arrows represent enzyme-catalyzed reactions. Next to the arrow, the corresponding EC number of the enzymatic reaction is indicated. A circled plus denotes an enzymatic reaction which could be assigned to a gene in the genome of Trichoderma reesei. A circled minus indicates that no annotated gene could be found in the currently published genome.

(a) The extracted ion chromatograms (EIC) of an HPLC-MS analysis with a mass of 222,098 atomic mass units (amu) are shown. This mass corresponds to the mass of the [GlcNAc+H]+ ion and to that of the [ManNAc+H]+ ion. The retention times (RT) of GlcNAc (12.988 rpm) and ManNAc (12.288 min) were determined using pure standards of both substances and are indicated by a vertical line in the chromatogram. (1) Chromatogram of the in vitro enzymatic reaction with GST fusion proteins of GlcNAc 2-epimerase and NeuNAc synthase, which were expressed in E. coli. (2) Chromatogram of the enzymatic reaction with the cell-free extract of the transgenic strain PEC/PSC1. (3) Chromatogram of the reaction with the cell-free extract of the parent strain QM9414 as a negative control.

(b) Illustrated are the EICs at a mass of 310.1134 amu, which corresponds to the mass of the [NeuNAc+H]+ ion and can be detected at a retention time of 8.345 min. The chromatograms (1), (2) and (3) were obtained with the same samples as described in section (a), wherein chromatogram (2) is amplified 10-fold and chromatogram (3) is amplified 1,000-fold in relation to chromatogram (1). (ad 1) includes the mass spectrum pertaining to chromatogram (1) at a retention time of 8.345 min. (ad 2) shows the mass spectrum of chromatogram (2) at a retention time of 8.348 min.

Figure 3A:
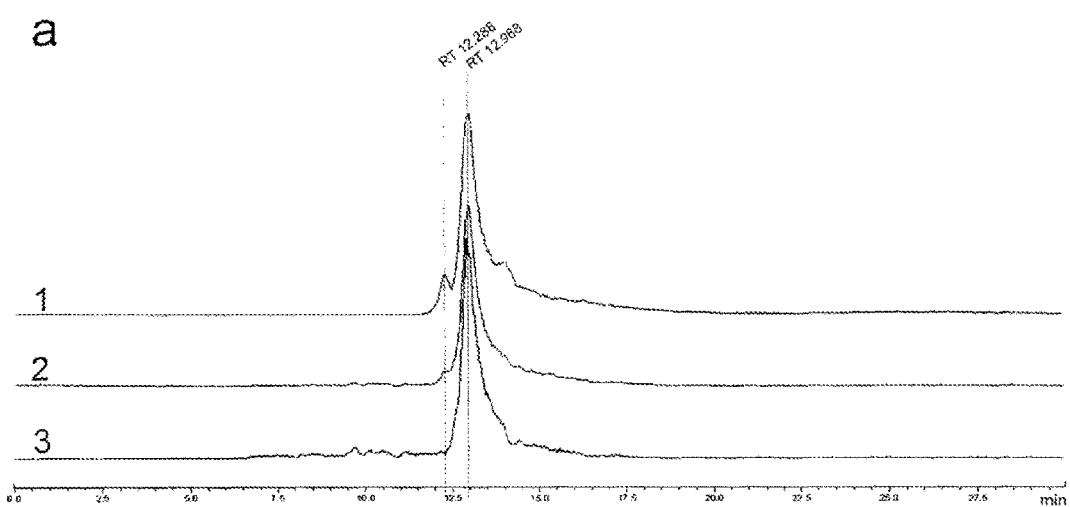
Figure 3B:
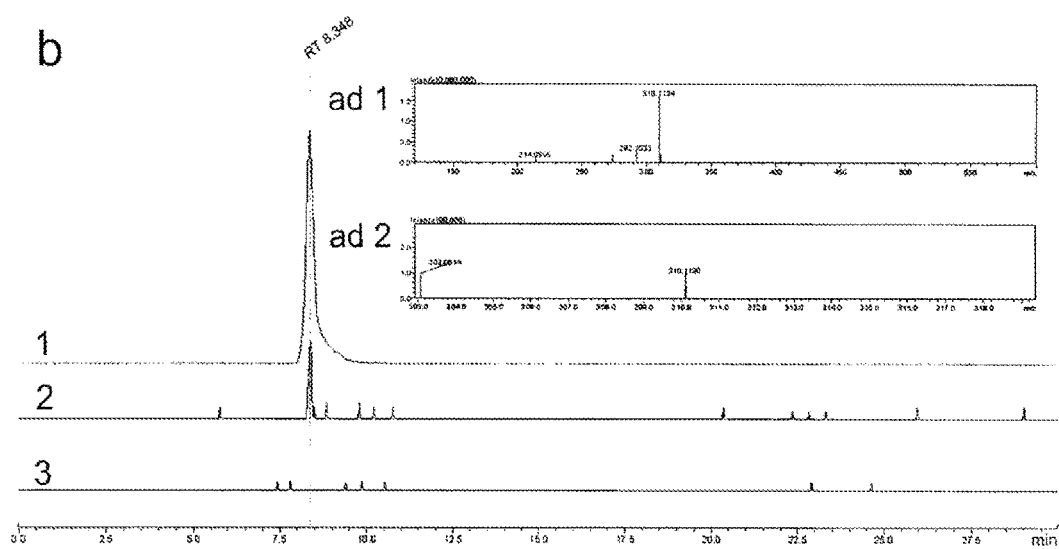

FIGS. 3a and 3b show the in vivo production of NeuNAc in the transgenic *T. reesei* strain PEC/PSC1 after cultivation on GlcNAc for 66 h.

(a) Illustrated are the EICs of the HPLC-MS analysis with a mass of 222.097 amu (the [GlcNAc+H]+ ion and the [ManNAc+H]+ ion). The retention time (RT) of GlcNAc (12.988 min) and ManNAc (12.288 min) was determined using pure standards of both substances and is indicated by a vertical line in the chromatogram. (1) Chromatogram of the in vitro enzymatic reaction with GST fusion proteins of GlcNAc 2-epimerase and NeuNAc synthase, which were expressed in *E. coli*. (2) Chromatogram of the cell-free extract of the transgenic strain PEC/PSC1 (3) Chromatogram of the cell-free extract of the parent strain QM9414 as a negative control.

(b) Illustrated are the EICs with a mass of 310.1134 amu, which corresponds to the mass of the [NeuNAc+H]+ ion and can be detected at a retention time of 8.345 min. The chromatograms (1), (2) and (3) were obtained with the same samples as described in section (a), wherein chromatogram (2) is amplified 100-fold and chromatogram (3) is amplified 1,000-fold in relation to chromatogram (1). (ad 1) includes the mass spectrum pertaining to chromatogram (1) at a retention time of 8.345 min. (ad 2) shows the mass spectrum of chromatogram (2) at a retention time of 8.348 min.

EXAMPLE

Materials and Methods

Strains and Culture Conditions

*Trichoderma reesei* (*Hypocrea jecorina*) QM9414 (ATCC 26921) was used as the parent strain in this example and was cultured on malt extract agar.

Mycelia for the in vitro enzymatic reactions were obtained from cultures of the strains set up in 1,000 mL Erlenmeyer flasks with 200 mL of 3% (w/v) malt extract. The flasks were inoculated with 10^8 conidia per liter and the cultivation was carried out at 30° C. and 250 rpm for 40 h. The cultivation of *T. reesei* on colloidal chitin was performed in 1,000 mL Erlenmeyer flasks each containing 200 ml of Mandels-Andreotti medium including 1% (w/v) colloidal chitin and 0.1% (w/v) bacto peptone. The inoculation was performed with 10^8 conidia per liter and the incubation was carried out at 30° C. and 250 rpm for 90 h.

For the in vivo production of NeuNAc, the corresponding *T. reesei* strains were directly cultured in 250 mL of Mandels-Andreotti medium containing 1% (w/v) GlcNAc at 30° C. and 250 rpm for 66 h (inoculation with 10^8 spores/liter).

Synthetic Genes and Plasmid Construction

The synthetic gene tbage was generated based on the protein sequence of *Anabaena* sp. CH1 GlcNAc 2-epimerase (GenBank: ABG57042) by translating the protein sequence into a DNA sequence using the software GeneOptimizer® (Geneart, Germany). In this process, the DNA sequence was optimized with respect to the codon usage of *T. reesei* (Table 1):

>tbage
(SEQ ID NO: 3)
tctagaatgggcaagaacctccaggccctggcccagctctacaagaacgc cctcctcaacgacgtcctgcccttctgggagaaccacagcctcgacagcg agggcggctacttcacctgcctcgaccgccagggcaaggtctacgacacc gacaagttcatctggctccagaaccgccaggtctggaccttcagcatgct ctgcaaccagctggagaagcgcgagaactggctcaagatcgcccgcaacg gcgccaagttcctcgcccagcacggccgcgacgacgagggcaactggtac tttgccctgacccgcggcggcgagcctctggtccagccctacaacatctt cagcgactgcttcgccgccatggccttcagccagtacgccctcgccagcg gcgaggagtgggccaaggacgtcgccatgcaggcctacaacaacgtcctc cgccgcaaggacaaccccaagggcaagtacaccaagacctaccccggcac ccgccccatgaaggccctggctgtccccatgatcctcgccaacctcaccc tggagatggagtggctcctcccccaggagaccctggagaacgtcctcgcc gccaccgtccaggaggtcatgggcgacttcctcgaccaggagcagggcct catgtacgagaacgtcgcccccgacggcagccacatcgactgcttcgagg gccgcctcatcaacccccgccacggcatcgaggccatgtggttcatcatg gacatcgcccgccgcaagaacgacagcaagaccatcaaccaggccgtcga cgtcgtcctca-acatcctcaacttcgcctgggacaacgagtacggcggc ctctactacttcatggacgccgccggccaccccccccagcagctggagtg ggaccagaagctctggtgggtccacctggagagcctcgtcgccctcgcca tgggctaccgcctcaccggccgcgacgcctgctgggcctggtatcagaag atgcacgactacagctggcagcacttcgccgaccctgagtacggcgagtg gttcggctacctcaaccgccgaggcgaggtcctcctcaacctcaagggcg gcaagtggaagggctgcttccacgtccccgcgccatgtacctctgctgg cagcagttcgaggccctcagctaatgcat

In an analogous manner, the synthetic gene tneub was generated which is based on the protein sequence of the NeuNAc synthase from *Campylobacter jejuni* NCTC11168 and whose DNA sequence was also adapted to the codon usage of *T. reesei*:

>tneub
(SEQ ID NO: 4)
tctagaatgcagatcaagatcgacaagctcaccatcagccagaagaaccc cctcatcatccccgagatcggcatcaaccacaacggcagcctggagatcg ccaagctcatggtcgacgccgccaagcgagccggcgccaagatcatcaag caccagacccacatcgtcgaggacgagatgagccaggaggccaagaacgt catccccggcaacgccaacatcagcatctacgagatcatggagcagtgcg ccctcaactacaaggacgagctggccctcaaggagtacgtcgagaagcag ggcctcgtctacctcagcacccccttcagccgcgccgccgccaaccgcct ggaggacatgggcgtcagcgcctacaagatcggcagcggcgagtgcaaca actaccccctgatcaagcacatcgcccagttcaagaagcccatgatcatc agcaccggcatgaacagcatcgagagcatcaagcccaccgtcaagatcct ccgcgactacgagatccccttcgtcctcctgcacaccaccaacctctacc ccaccccagccacctcgtccgcctccaggccatgctggagctgtacaag gagttcaactgcctctacggcctcagcgaccacacgacgaacaacctcgc ctgcatcggcgccatcgccctcggcgccagcgtcctggagcgccacttca -continued ccgacaccatggaccgcaagggccccgacatcgtctgcagcatggacgag agcaccctcaaggacctcatcaaccagacccaggagatggtcctcctccg cggcgacaacaacaagaaccccctgaaggaggagcaggtcaccatcgact tcgccttcgccagcgtcgtcagcatcaaggacatcaagaagggcgagatc ctcagcatggacaacatctgggtcaagcgcccagcaagggcggcatcag cgccaaggacttcgaggccatcctcggcaagcgcgccaagaaggacatca agaacaacatccagctcacctggcacgacttcgagtaatgcat

For the construction of the plasmids pMS-PEC and pMS-PSC, the synthetic genes tbage and tneub were cut from their production plasmid using XbaI/NsiI restriction digestion and were inserted into the plasmid pRLM$_{ex30}$ (Mach, R. L. et al., 1994, Curr. Genet. 25:567-70), wherein the hph gene located between the XbaI and the NsiI restriction site was replaced by tbage and tneub, respectively.

For the construction of pGEX-epi and pGEX-syn, the plasmid pGEX4T-2 (GE Healthcare, UK) was digested with EcoRI and XhoI. A double-stranded DNA consisting of the oligomeric nucleotides GEXfw and GEXrev (Table 1) was inserted into the open pGEX4T-2, whereby the plasmid pGEX-MS was obtained and the new restriction sites XbaI and NsiI were generated. tbage tneub were introduced into pGEX-MS via the restriction sites XbaI/NsiI, which resulted in the formation of the plasmids pGEX-epi and pGEX-syn.

TABLE 2

Nucleotide sequences of the oligomers used

| Name | Sequence (5'→3') | Usage |
|---|---|---|
| NANASfw | GTGGTGTGCAGGAGGACGAA (SEQ ID NO: 5) | qPCR tneub |
| NANASrev | CAAGCACATCGCCCAGTTCAAG (SEQ ID NO: 6) | qPCR tneub |
| ManEfw | GCGATCTTGAGCCAGTTCTC (SEQ ID NO: 7) | qPCR tbage |
| ManErev | GCTACTTCACCTGCCTCGAC (SEQ ID NO: 8) | qPCR tbage |
| GEX-MSfw | AATTCCTTCTAGAGATATGCATC (SEQ ID NO: 9) | construction of pGEX-MS |
| GEX-MSrev | TCGAGATGCATATCTCTAGAAGG (SEQ ID NO: 10) | construction of pGEX-MS |
| pkifw R | CTGCGACACTCAGAACATGTACGT (SEQ ID NO: 11) | qPCR pki cDNA |
| pkifw D | GCTCTGCTTGGAACCTGATTGA (SEQ ID NO: 12) | qPCR pki DNA |
| pkirev | GGTCTGGTCGTCCTTGATGCT (SEQ ID NO: 13) | qPCR pki |
| sar1fw | TGGATCGTCAACTGGTTCTACGA (SEQ ID NO: 14) | qPCR sari |
| sar1rev | GCATGTGTAGCAACGTGGTCTTT (SEQ ID NO: 15) | qPCR sari |

Protoplast Transformation of *T. reesei*

The protoplast transformation of *T. reesei* was carried out as mentioned in a previous article (Gruber, F. et al., 1990. Curr. Genet. 18, 71-6). A total amount of 10 μg of DNA was used per transformation. In a co-transformation, pMS-PEC (4 μg) and pMS-PSC (4 μg) were transformed together with the plasmid pHylox2 (2 μg) which mediates a resistance to hygromycin B. Recombinant strains were selected for hygromycin B resistance.

RNA Analysis

RNA extraction, reverse transcription and qPCR were performed as described in a previous article. Oligomer nucleotide sequences which were employed as primers are given in Table 1. Sar1 was used as a reference gene for the normalization of the RT-qPCR. The primers ManEfw and ManErev were used for the gene tbage in the qPCR at an optimal elongation temperature of 64° C. and with 2 mM MgCl$_2$. The primers NANAfw and NANArev were used for the gene tneub in the qPCR at an optimal elongation temperature of 64° C. For the pki gene, the primers pkifwR and pkirev were used in the qPCR at an optimal elongation temperature of 64° C. Data analysis was carried out using REST 2008.

DNA Analysis

Genomic DNA was isolated from the fungal mycelium, as described in a previous article. The hybridization and detection was carried out according to standard operating procedures using the DIG High Prime DNA Labeling and Detection Starter Kit II (Roche, Switzerland). The qPCR of genomic DNA was performed using about 50 ng of genomic template DNA. The same primers as in the RNA analysis were used for the genes tbage and tneub. pki served as a reference gene and was amplified with the primers pkifwD and pkirev at an elongation temperature of 64° C.

Glutathione S-Transferase (GST) Fusion Proteins

GST fusion proteins of GlcNAc 2-epimerase (GST: epi) and NeuNAc synthase (GST: syn) were produced by expression of the plasmids pGEX-epi and pGEX-syn in *E. coli* BL21 (DE3) cells. According to the standard operating protocol, the fusion proteins were purified with the aid of GSTrap™FF columns having a column volume of 1 mL (GE Healthcare).

Enzymatic Reaction with Cell-Free Extracts

Harvested mycelia were first ground in liquid nitrogen to give a fine powder and then immediately resuspended in a 0.1 M bicine buffer (pH 8) containing protease inhibitors (2 μM of leupeptin, 1 μM of pepstatin A, 10 μM of PMSF) (0.3 g of mycelial powder/1 mL of buffer). The suspension was further lysed using an ultrasonic probe Sonifier® 250 Cell Disruptor (Branson, U.S.) (settings: power 40%, duty cycle 50%, 20 s action, 40 s pause, 10 cycles) and insoluble components were separated by centrifugation (10 min, 13,000×g, 4° C.). The whole supernatant was used in the enzymatic reaction. The enzymatic reaction was carried out in a similar manner as described by Vann et al. (Vann, W. F., et al., 1997, Glycobiology 7:697-701). The reaction for detecting the activity of GlcNAc 2-epimerase involves 10 mM GlcNAc, 0.2 mM ATP, 100 mM bicine buffer (pH 8) and 10-40 μL of cell-free extract in a total volume of 100 μL. The reaction for detecting the activity of NeuNAc synthase involves 10 mM ManNAc, 10 mM PEP, 12.5 mM MnCl$_2$, 100 mM bicine buffer (pH 8) and 10-40 μL of cell-free extract in a total volume of 100 μL. The combined reaction for detecting the activity of both GlcNAc 2-epimerase and NeuNAc synthase involves 10 mM GlcNAc, 10 mM PEP, 12.5 mM MnCl$_2$, 100 mM bicine buffer (pH 8) and 40 μL of cell-free extract in a total volume of 100 μL. All reactions were incubated for 60 min at 37° C., heat-inactivated for 10 min at 85° C. and then analyzed by HPLC. 5 μL (1 μg/μL) each of the GST-fusion proteins GST:epi and GST:syn were used a positive control in the enzymatic reaction instead of using cell-free extracts.

Chitinase Enzymatic Reaction

In this reaction, the release of GlcNAc from the polymer chitin is measured. Chitin was employed both as raw chitin from crab shells and as colloidal chitin in a 30 mM phosphate buffer (pH 4.7). 5, 10 or 50 μL of the culture supernatant were measured in a total volume of 1.5 mL. The reaction was incubated for 20 h at 37° C. and then heat-inactivated for 10 min at 90° C. The formation of GlcNAc was measured in the HPLC.

NeuNAc Detection in Cell-Free Extracts

Harvested mycelium of *T. reesei* was ground in liquid nitrogen to give a fine powder and resuspended in bidistilled water (0.3 g of mycelial powder/1 ml of water). The suspension was further lysed with an ultrasonic probe Sonifier® 250 Cell Disruptor (Branson, U.S.) (settings: Power 40%, duty cycle 50%, 20 s action, 40 s pause, 10 cycles) and insoluble components were separated by centrifugation (10 min, 13,000×g, 4° C.). The supernatant was filtered through a 0.45 μm filter and analyzed by HPLC-MS.

HPLC-MS Analysis

The formation of NeuNAc and ManNAc in the enzymatic reaction as well as in the cell-free extract was measured in a HPLC-MS (IT-TOF-MS) (Shimadzu, Japan) using a Rezex™ RHM monosaccharide H$^+$ column (8%, 300×7.8 mm) (Phenomenex, USA). The mobile phase consisted of water containing 0.1% (v/v) of trifluoroacetic acid and the flow was set to 0.6 mL/min. The column temperature was 80° C. and 10 μL of sample were loaded onto the column. Detection was performed in the ESI$^+$ mode and a scanning range of 60 to 600 amu was covered.

Results

In Silico Analysis of a NeuNAc Biosynthesis Pathway in *T. reesei*

At present, there is no evidence in the literature that NeuNAc can be produced naturally in *Trichoderma reesei*. Therefore, the known metabolic reactions leading to the production of NeuNAc were verified in silico and it was checked whether they also occur in *T. reesei*. FIG. 1 illustrates the presently known enzyme-catalyzed processes which lead to the formation of NeuNAc using the biopolymer chitin as a starting substance. Present in *Trichoderma* are enzymes which are required for catabolizing chitin. The first step from chitin to the monomer GlcNAc is catalyzed by chitinases (3.2.1.14). Furthermore, the activity of a hexokinase (EC 2.7.1.1), a GlcNAc 6-phosphate deacetylase (EC 3.5.1.25) and a glucosamine-6-phosphate deaminase (EC 3.5.99.6) is required to catabolize chitin, so that fructose-6-phosphate may eventually enter the glycolytic pathway. At least one potential enzyme in each case can be found in the annotated genome of *T. reesei* (Table 3). Furthermore, genes can be found that are responsible for the biosynthesis of chitin, including a phosphoacetylglucosamine mutase (EC 5.4.2.3), an UDP-N-GlcNAc diphosphorylase (EC 2.7.7.23) and a plurality of chitin synthases (EC 2.4.1.16). However, no genes are annotated in the genome of *T. reesei* that are responsible for the synthesis of ManNAc (EC 5.1.3.8 in bacteria, EC 5.1.3.4 in mammals) or for the synthesis of NeuNAc (EC 2.5.1.6. in bacteria, EC 2.7.1.60, EC 2.5.1.57, EC 3.1.3.29 in mammals).

TABLE 3

Candidate genes for the metabolic reactions of chitin and GlcNAc which are annotated in the genome of *T. reesei*.

| EC number | Name | Protein identity |
|---|---|---|
| EC 3.2.1.14 | Chitinase | 2735, 43873, 53949, 62645, 62704, 66041, 68347, 72339, 80833, 81598, 104401, 110317, 119859, 123354, 124043 |
| EC 2.7.1.1 | Hexokinase | 56129, 73665, 79677 |
| EC 3.5.1.25 | GlcNAc-6-phosphate deacetylase | 79671 |
| EC 3.5.99.6 | Glucosamine-6-phosphate deaminase | 49898 |
| EC 5.4.2.3 | Phosphoacetylglucosamine mutase | 80994 |
| EC 2.7.7.23 | UDP-N-GlcNAc diphosphorylase | 79568 |
| EC 2.4.1.16 | Chitin synthase | 51492, 55341, 58188, 71563, 112271, 122172 |

A Gene Cluster for the Catabolic Conversion of GlcNAc in *Trichoderma reesei*

During the in silico analysis of the degradation pathways for GlcNAc, three candidate genes (estExt_GeneWisePlus.C_140427, est-tExt_GeneWisePlus.C_140421, estExt_Genewise1.C_140432) could be found which encode a hexokinase, a GlcNAc-6-phosphate deacetylase and glucosamine-6-phosphate deaminase and are all located in close proximity to one another in the genome of *T. reesei* (location in the genome on "scaffold 14": 714385-729984). Similar clusters are also present in other filamentous fungi, such as *Neurospora crassa* or *Aspergillus nidulans*, which is indicative of a conserved cluster for the catabolism of GlcNAc.

The hexokinase (Protein ID 79677) that is annotated in the genome of *T. reesei* can therefore be further specified as GlcNAc kinase (EC 2.7.1.59), analogous to the annotation and characterization in *Candida albicans* (39). Furthermore, the gene (estExt_GeneWisePlus.C_140419), which is located adjacent to the GlcNAc-6-phosphate deacetylase (estExt_GeneWisePlus.C_140421), may also pertain to the cluster as a homologue of this gene in *Neurospora crassa* is annotated as ß-N-acetylglucosaminidase (*N. crassa* OR74A (NC10): Supercontig. 6: 560844-564980) is annotated.

Construction of Expression Vectors

A two-enzyme strategy was chosen for the production of NeuNAc in *Trichoderma*, wherein the first enzymatic step is catalyzed by a GlcNAc 2-epimerase (EC 5.1.3.8) and the second by a NeuNAc synthase (EC 2.5.1.99). The protein sequence of the GlcNAc 2-epimerase from *Anabaena* sp. CH1 (GenBank: ABG57042) and, for the NeuNAc synthase, the protein sequence of *Campylobacter jejuni* NCTC11168 (Cj1141) were selected as candidates. The protein sequences were translated into DNA sequences by means of the software GeneOptimizer® (Geneart) and the codon usage was adapted to that of *T. reesei* (Table 1). The resulting synthetic genes were designated as tbage and tneub.

The coding sequences were inserted into the plasmid pRLMex30, wherein the coding sequence for the hph gene was substituted in this plasmid. Thus, both genes were under the control of the constitutive pki promoter and the cbh2 terminator (plasmid pMS-PEC with tbage and plasmid pMS-PSC with tneub).

In order to be able to also express both genes under an inducible system, the pki promoter was replaced by the xyn1 promoter (plasmid pMS-XEX with tbage and plasmid pMS-XSC with tneub).

TABLE 4

Comparison of an inducible promoter system (xyn1) and a constitutive promoter system (pki)

| | | Genomic DNA | | Transcript formation | | Enzymatic activity | |
|---|---|---|---|---|---|---|---|
| Strain | Promoter | Epimerase | Synthase | Epimerase | Synthase | Epimerase | Synthase |
| XEX5 | xyn1 | + | n.d. | + | n.d. | − | n.d. |
| XEX11 | xyn1 | + | n.d. | + | n.d. | − | n.d. |
| XSC3 | xyn1 | n.d. | + | n.d. | + | n.d. | − |
| XSC13 | xyn1 | n.d. | + | n.d. | + | n.d. | − |
| PEC11 | pki | + | n.d. | + | n.d. | + | n.d. |
| PEC15 | pki | + | n.d. | + | n.d. | + | n.d. |
| PEC17 | pki | + | n.d. | + | n.d. | + | n.d. |
| PSC15 | pki | n.d. | + | n.d. | + | n.d. | + |
| PSC16 | pki | n.d. | + | n.d. | + | n.d. | + |
| PSC17 | pki | n.d. | + | n.d. | + | n.d. | − |
| XEX/XSC1 | xyn1 | + | + | + | + | − | − |
| XEX/XSC5 | xyn1 | + | + | + | + | − | − |
| PEC/PSC1 | pki | + | + | + | + | + | + |
| PEC/PSC10 | pki | + | + | + | + | + | − |

(n.d. = not determined, + present, − absent)

To produce *Trichoderma reesei* strains that are capable of producing NeuNAc, the parent strain QM9414 was transformed with various combinations of the plasmids pMS-PEC, pMS-PSC, pMS-XEX as well as pMS-XSC and pMS-Hylox2 (including the selection marker hph between two loxP sequences). The plasmids containing the genes tbage and tneub were transformed both individually and in a combination of tneub/tbage.

Selected transformants were examined with respect to integration of the transformed DNA in the genome as well as transcript formation and enzymatic activity of GlcNAc 2-epimerase and NeuNAc synthase. The results are shown in Table 4. It can be seen that while there was a detectable transcript formation with the xyn1 promoter, no enzymatic activity of the two heterologously expressed enzymes could be detected. Work was therefore continued exclusively with those strains in which expression occurred under the control of the pki promoter.

The two strains PEC/PSC1 and PEC/PSC10 were further examined with respect to their genomic copy number ratio of tbage and tneub. Table 5 shows the results of this investigation.

TABLE 5

Comparison of gene transcription and gene copy number between two transgenic strains of *T. reesei*

| Designation of gene | Transcript ratio PEC/PSC1/PEC/PSC10 Median [95% CI] | Copy ratio PEC/PSC1/PEC/PSC10 median [95% CI] |
|---|---|---|
| tbage | 2.021 [1.589-2.836] | 1.810 [1.376-2.585] |
| tneub | 0.479 [0.385-0.622] | 0.400 [0.320-0.492] |

The strain PEC/PSC1 exhibits a transcription of the tbage gene that is approximately 2-fold higher than that of the strain PEC/PSC10. In contrast, the strain PEC/PSC10 exhibits an about 2-fold higher transcription of the gene family tneub than the strain PEC/PSC1. These difference in transcription levels can be explained by the different copy numbers of the two genes in the genome of both strains. The ratio of the copy number in both strains was measured by qPCR of genomic DNA, wherein the gene encoding the pyruvate kinase (pki) was used as reference gene. The copying conditions in both strains equaled the transcription ratios, which leads to the fact that the different transcription ratios can be explained with the copy number ratio and each copy of the gene is apparently transcribed with the same efficiency (Table 5).

Heterologous Protein Expression of GlcNAc 2-Epimerase and NeuNAc Synthase in *Trichoderma reesei*

Figure 2A:
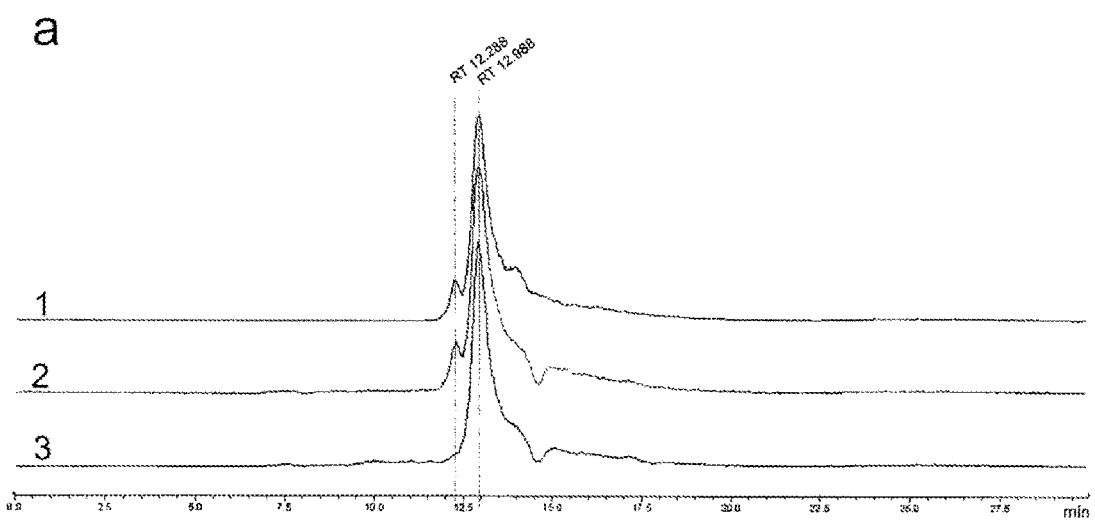
FIGS. 2a and 2b show the formation of NeuNAc in an in vitro reaction with heterologously expressed T. reesei protein in the transgenic strain PEC/PSC1 using the substrates GlcNAc, ATP and PEP.
Figure 2B:
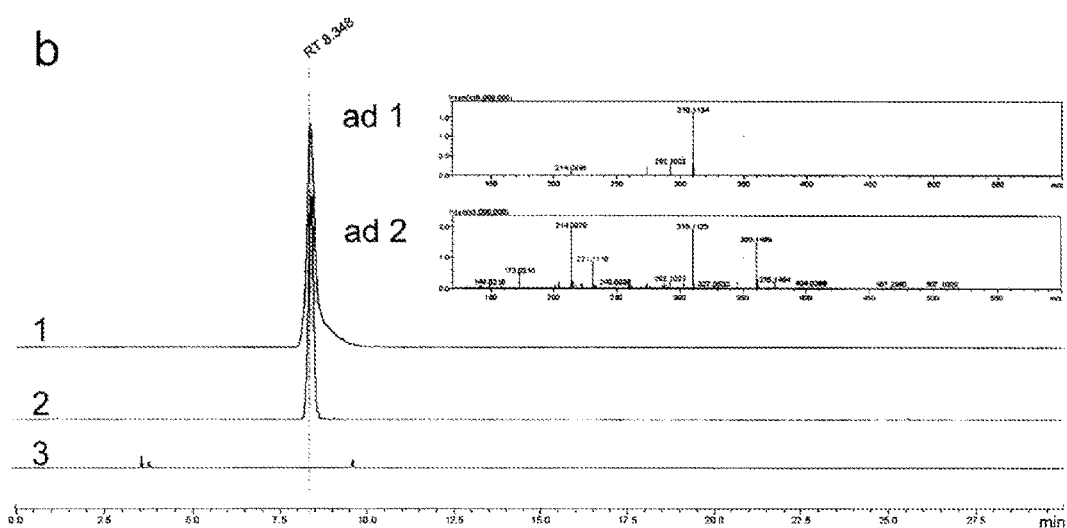

After the cultivation of the *Trichoderma reesei* strain, the cell-free extract was tested for the presence of GlcNAc 2-epimerase and NeuNAc synthase. The conversion of the substrates PEP and GlcNAc to form ManNAc and NeuNAc was measured subsequently to the addition of the cell-free enzyme-containing extract. The conversion reaction was analyzed by HPLC-MS and the corresponding chromatograms are shown in FIGS. 2a and 2b. In this conversion reaction, GST fusion proteins of GlcNAc 2-epimerase (tbage) and NeuNAc synthase (tneub), which are produced by expression in *E. coli*, were used as a positive control.

The formation of ManNAc and NeuNAc shows indicates that the two synthetic genes tbage and tneub are functionally expressed in *Trichoderma* (FIG. 2a2 and FIG. 2b2). Also, the positive control with the GST fusion proteins shows the formation of ManNAc and NeuNAc (FIG. 2a1 and FIG. 2b1). Neither ManNAc nor NeuNAc are formed in the enzymatic reaction when an extract of the original strain QM9414 is used. This result shows that no significant GlcNAc 2-epimerase activity is present in the parent strain. Furthermore, it was also exclusively tested for NeuNAc synthase activity in strain QM9414, wherein ManNAc and PEP were used as a substrate in the enzymatic reaction. Neither in this case any activity in the parent strain could be observed, which suggests that there is neither NeuNAc synthase activity nor GlcNAc 2-epimerase activity in natural isolates of *Trichoderma reesei*.

Growth of *Trichoderma reesei* on Colloidal Chitin and Release of GlcNAc

In order to investigate the hydrolysis of chitin to form the monomer GlcNAc, the *T. reesei* strain PEC/PSC1 was cultured on colloidal chitin as a carbon source. During the cultivation the increase in chitinase activity was monitored. After 90 h of cultivation time the chitinase activity reached its maximum and the supernatant was tested for the ability to hydrolyze chitin. The results are presented in Table 6. Colloidal chitin from crab shells yields ten times more GlcNAc than untreated chitin from crab shells. The GlcNAc thus released may be used as a starting substance for the production of NeuNAc with the strain PEC/PSC1.

TABLE 6

Chitinase activity induced by cultivation of the *T. reesei* strain PEC/PSC1 on 1% chitin.

| Substrate | Chitinase activity[a] [mU/ml] |
|---|---|
| crab-shell chitin | 2.7 ± 0.5 |
| colloidal crab-shell chitin | 25.0 ± 0.9 |

[a]1U: Release of 1 μmol of GlcNAc/min at 37° C.

In Vivo Formation of NeuNAc in *T. reesei*

In the following experiment it was to be determined whether the two heterogeneously expressed enzymes are also functional and capable of forming NeuNAc from their culture medium in vivo. For this experiment, the recombinant strain PEC/PSC1 was cultured on GlcNAc. The parent strain QM9414 was cultivated as a negative control. The mycelium of both strains was harvested and assayed for the presence of NeuNAc by means of HPLC-MS. The results are shown in FIGS. 3a and 3b.

The recombinant strain PEC/PSC1 produces ManNAc (FIG. 3a2) and NeuNAc (FIG. 3b2, 10 μg per g of dry biomass). This result indicates that NeuNAc can be produced in *T. reesei* by co-expression of two bacterial enzymes. The parental strain QM9414 shows neither a formation of NeuNAc nor of ManNAc (FIG. 3a3 and FIG. 3b3).

Summary of the Results

In this example, the introduction of an intracellular synthesis pathway for the production of NeuNAc in the fungus *Trichoderma reesei* has been demonstrated. To the best of our knowledge, this was the first time that an intracellular two-stage enzyme cascade was introduced into a filamentous fungus in order to produce a fine chemical such as NeuNAc. While *T. reesei* itself is not capable of producing NeuNAc, it is well capable of producing the important intermediate metabolite GlcNAc. This substance is released in the depolymerization process of the renewable raw material chitin (Table 6). Because of its saprophytic nature, *T. reesei* produces a plurality of chitinases (Table 3) and is capable of effectively degrading the polymer chitin to yield its monomer GlcNAc. The specific biosynthesis of NeuNAc starts with intermediates of the chitin metabolic pathway (GlcNAc or UDP-GlcNAc) (see FIG. 1) which are available in *T. reesei*. However, no genes can be found in this organism that are similar to genes encoding an UDP-GlcNAc 2-epimerase, a ManNAc kinase, a NeuNAc 9-phosphate synthase or a NeuNAc 9-phosphatase. For an alternative synthesis pathway for NeuNAc, as can be found in bacteria, the activity of a GlcNAc 2-epimerase and a NeuNAc synthase (FIG. 1) is required. No genes for this pathway are present in *Trichoderma reesei*.

The presence of NeuNAc on the surface of conidia has already been detected in *Aspergillus fumigatus*, while NeuNAc could not be detected on the conidia of the *Trichoderma reesei* strain QM9414. Neither the necessary enzymatic activity nor traces of ManNAc and NeuNAc could be detected in this strain. This indicates that naturally occurring *Trichoderma reesei* strains are not capable of synthesizing NeuNAc or ManNAc. Therefore, it is necessary to induce the corresponding enzymatic activities in this organism by means of heterologous expression in order to produce NeuNAc. The first enzyme in this cascade, a GlcNAc 2-epimerase, was obtained from *Anabaena* sp. This enzyme is well-characterized and requires a comparatively small amount of the cofactor ATP (20 μM) to develop to its maximum activity.

The second enzyme, a NeuNAc synthase, was obtained from *C. jejuni*. The codon usage of both genes was optimized with respect to the codon usage of *Trichoderma reesei* in order to improve the expression of the bacterial genes in the fungal host. The constitutive promoter of the pki gene on the one hand and the well-controllable promoter of the xyn1 gene on the other hand were chosen for the expression of the genes. Under the control of the xyn1 promoter no successful expression of the two genes could be achieved. Although it was shown that the genes are transcribed, no enzymatic activity could be detected. Under the control of the pki promoter the two heterologously expressed genes can not only be transcribed, but the corresponding enzymatic activity could also be detected. In a strain expressing both genes under the control of the constitutive pki promoter, the formation of NeuNAc could also be demonstrated in vivo. For this purpose, the fungus was cultured on the biopolymer chitin, which resulted in the release of the monomer GlcNAc. When cultivating the recombinant strain the production of NeuNAc could be detected in the mycelium (FIG. 3b2).

It was shown by the introduction of a two-stage enzyme cascade into *Trichoderma reesei* that the fungus had acquired the capability of producing NeuNAc. This example shows that high-quality fine chemicals can be produced from a renewable resource, as for instance from chitin. However, not only chitin, but also a variety of other carbon sources, such as cellulose and hemicelluloses, can be utilized by the saprophytic fungus *Trichoderma reesei* and underscore its potential in the application as a cell factory for the production of various chemicals.

The invention claimed is:

1. A method for producing N-acetylneuraminic acid (NeuNAc), comprising cultivating a fungal cell in the presence of an N-acetyl-D-glucosamine source,
wherein the fungal cell is of the genus *Trichoderma* and comprises a) a nucleic acid molecule or b) a set of two nucleic acid molecules,
wherein the nucleic acid molecule of a) and each of the nucleic acid molecules of the set b) comprise at least one constitutive promoter that is active in the genus *Trichoderma*, and wherein the nucleic acid molecule of a) further comprises a nucleic acid sequence encoding an N-acetylglucosamine 2-epimerase and an NeuNAc synthase operatively linked to one or more of said at least one promoter, or the set of two nucleic acid molecules of b) comprises a nucleic acid molecule encoding the N-acetylglucosamine 2-epimerase and a nucleic acid molecule encoding the NeuNAc synthase, each of said molecules comprising at least one promoter that is active in fungal cells of the genus *Trichoderma* operably linked to the sequence encoding N-acetylglucosamine 2-epimerase or N-acetylneuraminic acid synthase,
wherein the N-acetylglucosamine 2-epimerase is SEQ ID NO:1.

2. The method according to claim 1, wherein the N-acetyl-D-glucosamine source is chitin.

3. The method according to claim 1, wherein the fungal cell is of the species *Trichoderma reesei*.

4. The method according to claim 1, wherein said at least one promoter is selected from the group consisting of a promoter of a glycolytic gene, a promoter of translational elongation factor EF-1 alpha (tef1a), a promoter of actin (act), a promoter of Subunit IV of cytochrome c oxidase (cox4), a promoter of 1,6-beta-D-glucanase gene (neg1) and a promoter of secretion-associated RAS-related protein (sar1).

5. The method according to claim 4, wherein said at least one promoter is a promoter of the glycolytic gene, wherein the gene is selected from the group consisting of pyruvate kinase (pki), glyceraldehyde-3-phosphate dehydrogenase (gpd) and zwischenferment (zwf1).

6. The method according to claim 2, wherein the chitin is colloidal.

7. The method according to claim 2, wherein the chitin is crab-shell chitin.

8. The method according to claim 1, wherein said nucleic acid sequence encoding an NeuNAc synthase is SEQ ID NO:2.

9. The method according to claim 1, wherein said nucleic acid molecule of a) encoding an N-acetylglucosamine 2-epimerase and an NeuNAc synthase or the set of nucleic acid molecules of b) encoding the N-acetylglucosamine 2-epimerase and the N-acetylneuraminic acid synthase is codon-optimized for expression in the fungal cell.

10. A method for producing N-acetylneuraminic acid (NeuNAc), comprising cultivating a fungal cell in the presence of an N-acetyl-D-glucosamine source,
wherein the fungal cell is of the genus *Trichoderma* and comprises a) a nucleic acid molecule or b) a set of two nucleic acid molecules,
wherein the nucleic acid molecule of a) and each of the nucleic acid molecules of the set b) comprise at least one constitutive promoter that is active in the genus *Trichoderma*, and wherein the nucleic acid molecule of a) further comprises a nucleic acid sequence encoding an N-acetylglucosamine 2-epimerase and an NeuNAc synthase operatively linked to one or more of said at least one promoter, or the set of two nucleic acid molecules of b) comprises a nucleic acid molecule encoding the N-acetylglucosamine 2-epimerase and a nucleic acid molecule encoding the NeuNAc synthase, each of said molecules comprising at least one promoter that is active in fungal cells of the genus *Trichoderma* operably linked to the sequence encoding N-acetylglucosamine 2-epimerase or N-acetylneuraminic acid synthase,
wherein the NeuNAc synthase is SEQ ID NO:2.

11. The method according to claim 10, wherein the N-acetyl-D-glucosamine source is chitin.

12. The method according to claim 10, wherein the fungal cell is of the species *Trichoderma reesei*.

13. The method according to claim 10, wherein said at least one promoter is selected from the group consisting of a promoter of a glycolytic gene, a promoter of translational elongation factor EF-1 alpha (tef1a), a promoter of actin (act), a promoter of Subunit IV of cytochrome c oxidase (cox4), a promoter of 1,6-beta-D-glucanase gene (neg1) and a promoter of secretion-associated RAS-related protein (sar1).

14. The method according to claim 13, wherein said at least one promoter is a promoter of the glycolytic gene, wherein the gene is selected from the group consisting of pyruvate kinase (pki), glyceraldehyde-3-phosphate dehydrogenase (gpd) and zwischenferment (zwf1).

15. The method according to claim 11, wherein the chitin is colloidal.

16. The method according to claim 11, wherein the chitin is crab-shell chitin.

17. The method according to claim 10, wherein said nucleic acid sequence encoding an N-acetylglucosamine 2-epimerase is SEQ ID NO:1.

18. The method according to claim 10, wherein said nucleic acid molecule of a) encoding an N-acetylglucosamine 2-epimerase and an NeuNAc synthase or the set of nucleic acid molecules of b) encoding the N-acetylglucosamine 2-epimerase and the N-acetylneuraminic acid synthase is codon-optimized for expression in the fungal cell.

* * * * *

SEQUENCE LISTING

```
<160> NUMBER OF SEQ ID NOS: 15

<210> SEQ ID NO 1
<211> LENGTH: 1167
<212> TYPE: DNA
<213> ORGANISM: Artificial Sequence
<220> FEATURE:
<223> OTHER INFORMATION: N-Acetyl-D-Glukosamin-2-Epimerase

<400> SEQUENCE: 1
atgggcaaga acctccaggc cctggcccag ctctacaaga acgccctcct caacgacgtc      60
ctgcccttct gggagaacca cagcctcgac agcgagggcg gctacttcac ctgcctcgac     120
```

```
cgccagggca aggtctacga caccgacaag ttcatctggc tccagaaccg ccaggtctgg      180
accttcagca tgctctgcaa ccagctggag aagcgcgaga actggctcaa gatcgcccgc      240
aacggcgcca agttcctcgc ccagcacggc cgcgacgacg agggcaactg gtactttgcc      300
ctgacccgcg gcggcgagcc tctggtccag ccctacaaca tcttcagcga ctgcttcgcc      360
gccatggcct tcagccagta cgccctcgcc agcggcgagg agtgggccaa ggacgtcgcc      420
atgcaggcct acaacaacgt cctccgccgc aaggacaacc ccaagggcaa gtacaccaag      480
acctaccccg gcacccgccc catgaaggcc ctggctgtcc ccatgatcct cgccaacctc      540
accctggaga tggagtggct cctccccag gagaccctgg agaacgtcct cgccgccacc       600
gtccaggagg tcatgggcga cttcctcgac caggagcagg gcctcatgta cgagaacgtc      660
gcccccgacg gcagccacat cgactgcttc gagggccgcc tcatcaaccc cggccacggc      720
atcgaggcca tgtggttcat catggacatc gcccgccgca gaacgacag caagaccatc       780 aaccaggccg tcgacgtcgt cctcaacatc ctcaacttcg cctgggacaa cgagtacggc      840
ggcctctact acttcatgga cgccgccggc cacccccccc agcagctgga gtgggaccag      900 aagtctggt gggtccacct ggagagcctc gtcgccctcg ccatgggcta ccgcctcacc       960
ggccgcgacg cctgctgggc ctggtatcag aagatgcacg actacagctg gcagcacttc     1020
gccgaccctg agtacggcga gtggttcggc tacctcaacc gccgaggcga ggtcctcctc     1080
aacctcaagg gcggcaagtg gaagggctgc ttccacgtcc ccgcgccat gtacctctgc      1140 tggcagcagt tcgaggccct cagctaa                                          1167

<210> SEQ ID NO 2
<211> LENGTH: 1032
<212> TYPE: DNA
<213> ORGANISM: Artificial Sequence
<220> FEATURE:
<223> OTHER INFORMATION: N-Acetylneuraminsaure-Synthase

<400> SEQUENCE: 2
atgcagatca agatcgacaa gctcaccatc agccagaaga accccctcat catccccgag       60
atcggcatca accacaacgg cagcctggag atcgccaagc tcatggtcga cgccgccaag      120
cgagccggcg ccaagatcat caagcaccag acccacatcg tcgaggacga gatgagccag      180
gaggccaaga acgtcatccc cggcaacgcc aacatcagca tctacgagat catggagcag      240
tgcgccctca actacaagga cgagctggcc ctcaaggagt acgtcgagaa gcagggcctc      300
gtctacctca gcaccccctt cagccgcgcc gccgccaacc gctggagga catgggcgtc       360 agcgcctaca agatcggcag cggcgagtgc aacaactacc ccctgatcaa gcacatcgcc      420
cagttcaaga gcccatgat catcagcacc ggcatgaaca gcatcgagag catcaagccc       480
accgtcaaga tcctccgcga ctacgagatc cccttcgtcc tcctgcacac caccaacctc      540 tacccccaccc ccagccacct cgtccgcctc caggccatgc tggagctgta caaggagttc      600
aactgcctct acggcctcag cgaccacacg acgaacaacc tcgcctgcat cggcgccatc      660
gccctcggcg ccagcgtcct ggagcgccac ttcaccgaca ccatggaccg caagggcccc      720
gacatcgtct gcagcatgga cgagagcacc ctcaaggacc tcatcaacca gacccaggag      780
atggtcctcc tccgcggcga caacaacaag aaccccctga aggaggagca ggtcaccatc      840
gacttcgcct tcgccagcgt cgtcagcatc aaggacatca gaagggcga gatcctcagc      900 atggacaaca tctgggtcaa gcgccccagc aagggcggca tcagcgccaa ggacttcgag      960
```

| | |
|---|---|
| gccatcctcg gcaagcgcgc caagaaggac atcaagaaca acatccagct cacctgggac | 1020 |
| gacttcgagt aa | 1032 |

<210> SEQ ID NO 3
<211> LENGTH: 1178
<212> TYPE: DNA
<213> ORGANISM: Artificial Sequence
<220> FEATURE:
<223> OTHER INFORMATION: N-Acetyl-D-Glukosamin-2-Epimerase

<400> SEQUENCE: 3

| | |
|---|---|
| tctagaatgg gcaagaacct ccaggccctg gcccagctct acaagaacgc cctcctcaac | 60 |
| gacgtcctgc ccttctggga gaaccacagc ctcgacagcg agggcggcta cttcacctgc | 120 |
| ctcgaccgcc agggcaaggt ctacgacacc gacaagttca tctggctcca gaaccgccag | 180 |
| gtctggacct tcagcatgct ctgcaaccag ctggagaagc gcgagaactg gctcaagatc | 240 |
| gcccgcaacg gcgccaagtt cctcgcccag cacggccgcg acgacgaggg caactggtac | 300 |
| tttgccctga cccgcggcgg cgagcctctg gtccagccct acaacatctt cagcgactgc | 360 |
| ttcgccgcca tggccttcag ccagtacgcc ctcgccagcg gcgaggagtg ggccaaggac | 420 |
| gtcgccatgc aggcctacaa caacgtcctc cgccgcaagg acaaccccaa gggcaagtac | 480 |
| accaagacct accccggcac ccgccccatg aaggccctgg ctgtccccat gatcctcgcc | 540 |
| aacctcaccc tggagatgga gtggctcctc ccccaggaga ccctggagaa cgtcctcgcc | 600 |
| gccaccgtcc aggaggtcat gggcgacttc ctcgaccagg agcagggcct catgtacgag | 660 |
| aacgtcgccc ccgacggcag ccacatcgac tgcttcgagg ccgcctcat caaccccggc | 720 |
| cacggcatcg aggccatgtg gttcatcatg gacatcgccc ccgcaagaa cgacagcaag | 780 |
| accatcaacc aggccgtcga cgtcgtcctc aacatcctca acttcgcctg gacaacgag | 840 |
| tacggcggcc tctactactt catggacgcc gccggccacc cccccagca gctggagtgg | 900 |
| gaccagaagc tctggtgggt ccacctggag agcctcgtcg ccctcgccat gggctaccgc | 960 |
| ctcaccggcc gcgacgcctg ctgggcctgg tatcagaaga tgcacgacta cagctggcag | 1020 |
| cacttcgccg accctgagta cggcgagtgg ttcggctacc tcaaccgccg aggcgaggtc | 1080 |
| ctcctcaacc tcaagggcgg caagtggaag ggctgcttcc acgtccccg cgccatgtac | 1140 |
| ctctgctggc agcagttcga ggccctcagc taatgcat | 1178 |

<210> SEQ ID NO 4
<211> LENGTH: 1043
<212> TYPE: DNA
<213> ORGANISM: Artificial Sequence
<220> FEATURE:
<223> OTHER INFORMATION: N-Acetylneuraminsaure-Synthase

<400> SEQUENCE: 4

| | |
|---|---|
| tctagaatgc agatcaagat cgacaagctc accatcagcc agaagaaccc cctcatcatc | 60 |
| cccgagatcg gcatcaacca caacggcagc ctggagatcg ccaagctcat ggtcgacgcc | 120 |
| gccaagcgag ccggcgccaa gatcatcaag caccagaccc acatcgtcga ggacgagatg | 180 |
| agccaggagg ccaagaacgt catccccggc aacgccaaca tcagcatcta cgagatcatg | 240 |
| gagcagtgcg ccctcaacta caaggacgag ctggccctca ggagtacgt cgagaagcag | 300 |
| ggcctcgtct acctcagcac ccccttcagc cgcgccgccg ccaaccgcct ggaggacatg | 360 |
| ggcgtcagcg cctacaagat cggcagcggc gagtgcaaca actacccct gatcaagcac | 420 |
| atcgcccagt tcaagaagcc catgatcatc agcaccggca tgaacagcat cgagagcatc | 480 |

| | |
|---|---|
| aagcccaccg tcaagatcct ccgcgactac gagatcccct tcgtcctcct gcacaccacc | 540 |
| aacctctacc ccacccccag ccacctcgtc cgcctccagg ccatgctgga gctgtacaag | 600 |
| gagttcaact gcctctacgg cctcagcgac cacacgacga caacctcgc ctgcatcggc | 660 |
| gccatcgccc tcggcgccag cgtcctggag cgccacttca ccgacaccat ggaccgcaag | 720 |
| ggccccgaca tcgtctgcag catggacgag agcaccctca aggacctcat caaccagacc | 780 |
| caggagatgg tcctcctccg cggcgacaac aacaagaacc ccctgaagga ggagcaggtc | 840 |
| accatcgact tcgccttcgc cagcgtcgtc agcatcaagg acatcaagaa gggcgagatc | 900 |
| ctcagcatgg acaacatctg ggtcaagcgc cccagcaagg gcggcatcag cgccaaggac | 960 |
| ttcgaggcca tcctcggcaa gcgcgccaag aaggacatca gaacaacat ccagctcacc | 1020 |
| tgggacgact tcgagtaatg cat | 1043 |

```
<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
```

| | |
|---|---|
| gtggtgtgca ggaggacgaa | 20 |

```
<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
```

| | |
|---|---|
| caagcacatc gcccagttca ag | 22 |

```
<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
```

| | |
|---|---|
| gcgatcttga gccagttctc | 20 |

```
<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
```

| | |
|---|---|
| gctacttcac ctgcctcgac | 20 |

```
<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
```
aattccttct agagatatgc atc                                              23

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
tcgagatgca tatctctaga agg                                              23

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
ctgcgacact cagaacatgt acgt                                             24

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gctctgcttg gaacctgatt ga                                               22

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
ggtctggtcg tccttgatgc t                                                21

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
tggatcgtca actggttcta cga                                              23

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
gcatgtgtag caacgtggtc ttt                                              23